United States Patent [19]

Clavenna

[11] 4,159,195
[45] Jun. 26, 1979

[54] HYDROTHERMAL ALKALI METAL RECOVERY PROCESS

[75] Inventor: LeRoy R. Clavenna, Baytown, Tex.

[73] Assignee: Exxon Research & Engineering Co., Florham Park, N.J.

[21] Appl. No.: 864,061

[22] Filed: Dec. 23, 1977

Related U.S. Application Data

[63] Continuation-in-part of Ser. No. 762,531, Jan. 24, 1977, abandoned.

[51] Int. Cl.² ............................. C10J 3/06; C10J 3/54
[52] U.S. Cl. .................................... 48/197 R; 48/202; 48/210; 208/9; 252/412; 423/127
[58] Field of Search ..................... 48/197 R, 202, 210; 423/119, 127; 208/10, 9; 252/412, 420

[56] References Cited

U.S. PATENT DOCUMENTS

| | | | |
|---|---|---|---|
| 1,971,354 | 8/1934 | Scheidt et al. | 423/119 |
| 2,058,145 | 10/1936 | Folger | 423/119 |
| 2,141,132 | 12/1938 | Folger | 423/127 |
| 2,420,852 | 5/1947 | Archibald | 423/119 |
| 2,438,488 | 3/1948 | Anderson et al. | 423/119 |
| 3,033,647 | 5/1962 | Yamazaki | 423/203 |
| 3,664,809 | 5/1972 | Burk | 423/119 |
| 3,998,607 | 12/1976 | Wesselhoft et al. | 48/197 R |
| 4,048,285 | 9/1977 | Szepesi et al. | 423/127 |
| 4,057,512 | 11/1977 | Vadovic et al. | 48/197 R |

FOREIGN PATENT DOCUMENTS

108917 11/1957 U.S.S.R.

OTHER PUBLICATIONS

"Operation of Experimental Plant for Producing Alumina from Anorthosite", St. Clair et al., Bulletin 577, Bureau of Mines, 1959.
"A Study of the Reactions Between Power Station Fly Ash and CaO Under Hydrothermal Conditions", Silikaty, vol. 19, No. 3, pp. 193–202, 1975.
"Rate of Decomposition of Nepheline by the Hydrochemical Method", Zhurnal Prikladnoi Khimii, Sazhin et al., vol. 39, No. 12, pp. 2617–2622, 12, 1966.
"A Study of the Effects of Potassium on the Process of Decomposition of Aluminosilicates by the Hydrothermal Method", Bukhovets et al., Fiz. Khim. OSN, pp. 101–116, 1969.

*Primary Examiner*—S. Leon Bashore
*Assistant Examiner*—Peter F. Kratz
*Attorney, Agent, or Firm*—Yale S. Finkle

[57] ABSTRACT

In a coal gasification operation or similar conversion process carried out in the presence of an alkali metal-containing catalyst wherein solid particles containing alkali metal residues are produced, alkali metal constituents are recovered from the particles by treating them with a calcium or magnesium-containing compound in the presence of water. The treating process is carried out under conditions such that the calcium or magnesium-containing compound reacts with water insoluble constituents of the alkali metal residues such as alkali metal aluminosilicates to produce an aqueous solution containing water soluble alkali metal constituents. The aqueous solution is recycled to the gasification process where the alkali metal constituents serve as at least a portion of the alkali metal constituents which comprise the alkali metal-containing catalyst. The process permits increased recovery of alkali metal constituents, thereby decreasing the overall cost of the gasification process by reducing the amount of makeup alkali metal compounds necessary.

15 Claims, 1 Drawing Figure

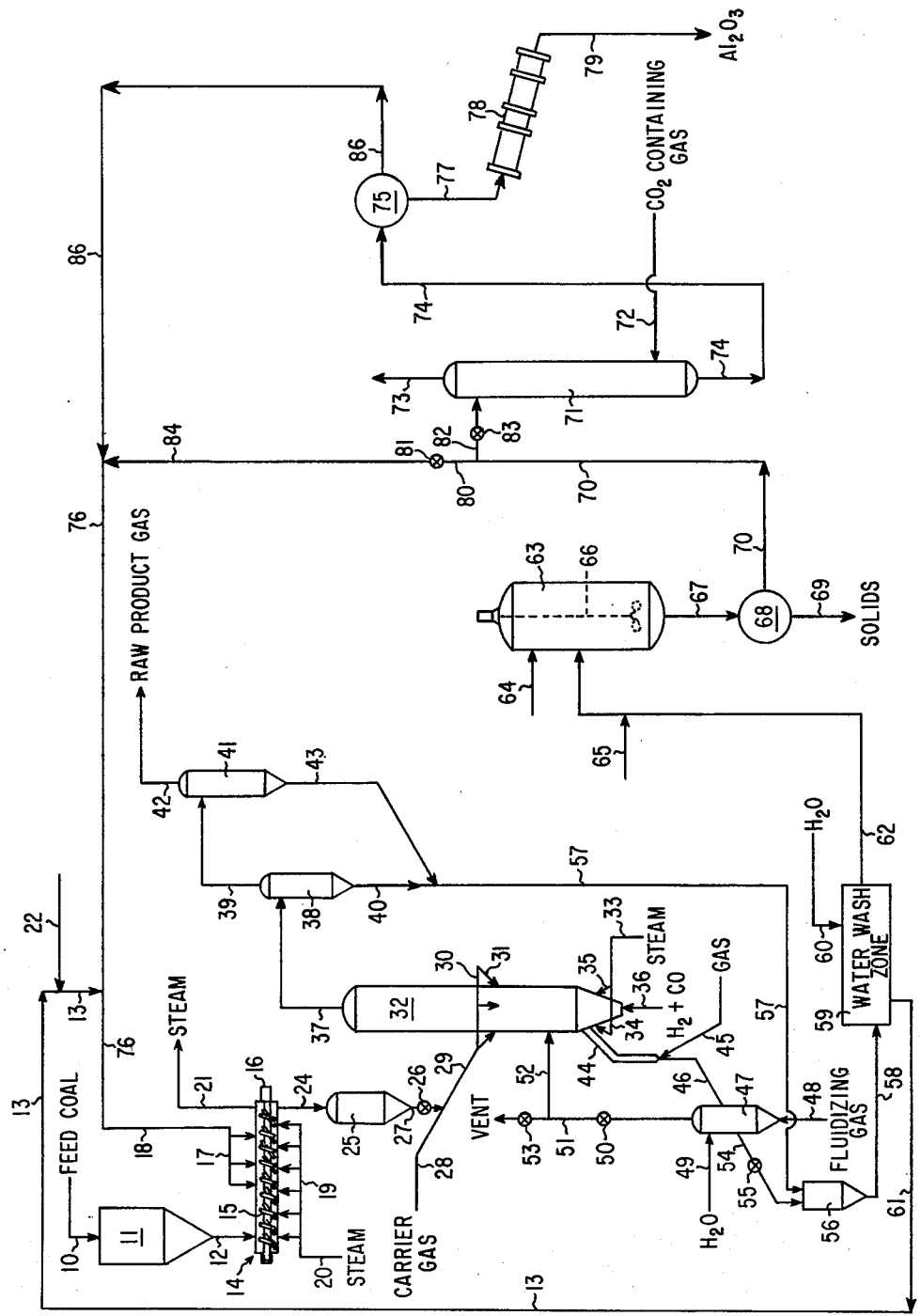

HYDROTHERMAL ALKALI METAL RECOVERY PROCESS

CROSS REFERENCE TO RELATED APPLICATIONS

This application is a continuation-in-part of Ser. No. 762,531, filed in the U.S. Patent and Trademark Office on Jan. 24, 1977 now abandoned.

BACKGROUND OF THE INVENTION

1. Field of the Invention

This invention relates to the conversion of coal and similar carbonaceous solids in the presence of alkali metal-containing catalysts and is particularly concerned with the recovery of alkali metal constituents from spent solids produced during coal gasification and similar operations and their reuse as constituents of the alkali metal-containing catalysts.

2. Description of the Prior Art

Potassium carbonate, cesium carbonate and other alkali metal compounds have been recognized as useful catalysts for the gasification of coal and similar carbonaceous solids. The use of such compounds in coal liquefaction, coal carbonization, coal combustion and related processes has also been proposed. To secure the higher reaction rates made possible by the presence of the alkali metal compounds it has been suggested that bituminous coal, subbituminous coal, lignite, petroleum coke, oil shale, organic wastes and similar carbonaceous materials be mixed or impregnated with potassium, cesium, sodium or lithium compounds, alone or in combination with other metallic constituents, before such materials are reacted with steam, hydrogen, oxygen or other agents at elevated temperatures to produce gaseous and/or liquid effluents. Studies have shown that a wide variety of different alkali metal compositions can be used for this purpose, including both organic and inorganic salts, oxides, hydroxides and the like.

In general the above-described studies indicate that cesium compounds are the most effective gasification catalysts followed by potassium, sodium and lithium compounds in that order. Because of the relatively high cost of cesium compounds and the low effectiveness of lithium compounds, most of the experimental work in this area that has been carried out in the past has been directed toward the use of compounds of potassium and sodium. This work has shown that the potassium compounds are substantially more effective than the corresponding sodium compounds. Attention has therefore been focused on the use of potassium carbonate.

Coal gasification processes and similar operations carried out in the presence of alkali metal compounds at high temperatures generally result in the formation of chars and alkali metal residues. The chars normally include unconverted carbonaceous constituents of the coal or other feed material and various inorganic constituents generally referred to as ash. It is generally advisable to withdraw a portion of the char from the reaction zone during gasification and similar operations in order to eliminate the ash and keep it from building up within the reaction zone or other vessels in the system. Elutriation methods and other techniques for separating char particles of relatively high ash content and returning particles of relatively low ash content to the reaction zone in order to improve the utilization of carbon in such processes have been suggested.

In gasification and other processes referred to above that utilize alkali metal-containing catalysts, the cost of the alkali metal constituents is a significant factor in determining the overall cost of the process. In order to maintain catalyst cost at reasonable levels, it is essential that the alkali metal constituents be recovered and reused. There have been proposals for the recovery of alkali metal constituents by leaching as they are withdrawn from the reaction zone with char during operations of the type referred to above. Studies indicate that these constituents are generally present in part as carbonates and other water soluble compounds which can be recovered by water washing. Experience has shown that only a portion of the potassium carbonate or other alkali metal constituents is normally recovered and that substantial quantities of makeup alkali metal compounds are therefore required. This adds appreciably to the cost of such operations.

SUMMARY OF THE INVENTION

The present invention provides an improved process for the recovery of alkali metal constituents from char particles produced during coal gasification and other conversion processes carried out in the presence of an alkali metal-containing catalyst. In accordance with the invention it has now been found that increased amounts of alkali metal constituents can be effectively recovered from particles containing alkali metal residues produced during coal gasification and related high temperature conversion processes by treating the particles with a calcium or magnesium-containing compound in the presence of water under conditions such that the calcium or magnesium-containing compound reacts with water insoluble compounds, such as alkali metal aluminosilicates, in the alkali metal residues to produce water insoluble precipitates and an aqueous solution containing water soluble alkali metal constituents. These alkali metal constituents are then used in the conversion process as at least a portion of the alkali metal constituents which comprise the alkali metal-containing catalyst. Preferably, such use is achieved by recycling the aqueous solution directly to the conversion process. If desired, however, the alkali metal constituents may first be recovered from the solution and then used in the conversion process. The aqueous solution produced in the treatment step may contain a substantial amount of water soluble alkali metal aluminates. If such is the case, it will normally be desirable to lower the pH of the solution to precipitate aluminum in the form of aluminum hydroxide before the solution is recycled to the conversion process.

The invention is based in part upon studies of the reactions that catalysts containing alkali metal constituents undergo during coal gasification and similar operations. Coal and other carbonaceous solids used in such operations normally contain mineral constituents that are converted to ash during the gasification process. Although the composition of ash varies, the principal constituents, expressed as oxides, are generally silica, alumina and ferric oxide. The alunina is usually present in the ash in the form of aluminosilicates. Studies have indicated that at least a portion of the alkali metal compounds, such as potassium carbonate, that are used as gasification catalyst constituents react with the aluminosilicates and other ash constituents to form alkali metal residues containing water soluble alkali metal compounds such as carbonates, sulfates, and the like, and water insoluble, catalytically inactive materials such as alkali metal aluminosilicates. Unless the alkali metal constituents in the insoluble alkali metal residues can be recovered, they are lost from the process and must be replaced by makeup alkali metal compounds. The process of this invention allows recovery of these alkali metal constituents and thereby decreases the costs incurred by utilizing large amounts of makeup alkali metal compounds. As a result the invention makes possible substantial savings in gasification and other conversion operations carried out in the presence of alkali metal-containing catalysts and permits the generation of product gases and/or liquids at significantly lower cost than would otherwise be the case.

BRIEF DESCRIPTION OF THE DRAWING

The drawing is a schematic flow diagram of a catalytic coal gasification process in which alkali metal constituents of the catalyst are recovered and reused in the process.

DESCRIPTION OF THE PREFERRED EMBODIMENTS

The process depicted in the drawing is one for the production of methane by the gasification of bituminous coal, subbituminous coal, lignite or similar carbonaceous solids with steam at high temperature in the presence of a carbon-alkali metal catalyst prepared by impregnating the feed solids with a solution of an alkali metal compound or a mixture of such compounds and thereafter heating the impregnated material to a temperature sufficient to produce an interaction between the alkali metal and the carbon present. It will be understood that the alkali metal recovery system disclosed is not restricted to this particular gasification process and that it can be employed in conjunction with any of a variety of other conversion processes in which alkali metal compounds or carbon-alkali metal catalysts are used to promote the reaction of steam, hydrogen, oxygen or the like with carbonaceous feed materials to produce a char, coke or similar solid product containing alkali metal residues from which alkali metal compounds are recovered for reuse as the catalyst or a constituent of the catalyst. It can be employed, for example, for the recovery of alkali metal compounds from various processes for the gasification of coal, petroleum coke, lignite, organic waste materials and similar solids feed streams which produce spent carbonaceous solids at temperatures below the ash fusion point. Other conversion processes with which it may be used include operations for the carbonization of coal and similar feed solids, for the liquefaction of coal and related carbonaceous feed materials, for the retorting of oil shale, for the partial combustion of carbonaceous feed materials, and the like. Such processes have been disclosed in the literature and will be familiar to those skilled in the art.

In the process depicted in the drawing, a solid carbonaceous feed material such as bituminous coal, subbituminous coal, lignite or the like that has been crushed to a particle size of about 8 mesh or smaller on the U.S. Sieve Series Scale is passed into line 10 from a feed preparation plant or storage facility that is not shown in the drawing. The solids introduced into line 10 are fed into a hopper or similar vessel 11 from which they are passed through line 12 into feed preparation zone 14. This zone contains a screw conveyor or similar device 15 that is powered by a motor 16, a series of spray nozzles or similar devices 17 for the spraying of alkali metal-containing solution supplied through line 18 onto the solids as they are moved through the preparation zone by the conveyor, and a similar set of nozzles or the like 19 for the introduction of steam into the preparation zone. The steam, supplied through line 20, serves to heat the impregnated solids and drive off the moisture. Steam is withdrawn from zone 14 through line 21 and passed to a condenser, not shown, from which it may be recovered for use as makeup water or the like. The majority of the alkali metal-containing solution is recycled through lines 13 and 76 from the alkali metal recovery section of the process, which is described in detail hereafter. Any makeup solution required may be introduced into line 13 via line 22.

It is preferred that sufficient alkali metal-containing solution be introduced into feed preparation zone 14 to provide from about 1 to about 50 weight percent of the alkali metal compound or mixture of such compounds on the coal or other carbonaceous solids. From about 1 to about 15 weight percent is generally adequate. The dried impregnated solid particles prepared in zone 14 are withdrawn through line 24 and passed to a closed hopper or similar vessel 25. From here they are discharged through a star wheel feeder or equivalent device 26 in line 27 at an elevated pressure sufficient to permit their entrainment into a stream of high pressure steam, recycle produce gas, inert gas or other carrier gas introduced into line 29 via line 28. The carrier gas and entrained solids are passed through line 29 into manifold 30 and fed from the manifold through feed lines 31 and nozzles, not shown in the drawing, into gasifier 32. In lieu of or in addition to hopper 25 and star wheel feeder 26, the feed system may employ parallel lock hoppers, pressurized hoppers, aerated standpipes operated in series, or other apparatus to raise the input feed solids stream to the required pressure level.

It is generally preferred to operate the gasifier 32 at a pressure between about 300 and about 2000 psig. The carrier gas and entrained solids will normally be introduced at a pressure somewhat in excess of the gasifier operating pressure. The carrier gas may be preheated to a temperature in excess of about 300° F. but below the initial softening point of the coal or other feed material employed. Feed particles may be suspended in the carrier gas in a concentration between about 0.2 and about 5.0 pounds of solid feed material per pound of carrier gas. The optimum ratio for a particular system will depend in part upon the feed particle size and density, the molecular weight of the gas employed, the temperature of the solid feed material and input gas stream, the amount of alkali metal compound employed and other factors. In general, ratios between about 0.5 and about 4.0 pounds of solid feed material per pound of carrier gas are preferred.

Gasifier 32 comprises a refractory-lined vessel containing a fluidized bed of carbonaceous solids extending upward within the vessel above an internal grid or similar distribution device not shown in the drawing. The bed is maintained in the fluidized state by means of steam introduced through line 33, manifold 34 and peripherally spaced injection lines and nozzles 35 and by means of recycle hydrogen and carbon monoxide introduced thorugh bottom inlet line 36. The particular injection system shown in the drawing is not critical and hence other methods for injecting the steam and recycle hydrogen and carbon monoxide may be employed. In some instances, for example, it may be preferred to introduce both the steam and recycle gases through multiple nozzles to obtain more uniform distribution of the injected fluid and reduce the possibility of channeling and related problems. The space velocity of the rising gases within the fluidized bed will normally be between about 300 and about 3000 volumes of steam and recycle hydrogen and carbon monoxide per hour per volume of fluidized solids.

The injected steam reacts with carbon in the feed material in the fluidized bed in gasifier 32 at a temperature within the range between about 800° F. and about 1600° F. and at a pressure between about 300 and about 2000 psig. Due to the equilibrium condition existing in the bed as a result of the presence of the carbon-alkali metal catalyst and the recycle hydrogen and carbon monoxide injected near the lower end of the bed, the reaction products will normally consist essentially of methane and carbon dioxide. Competing reactions, which in the absence of the catalyst and the recycle gases would ordinarily tend to produce additional hydrogen and carbon monoxide, are suppressed. The ratio of methane to carbon dioxide in the raw product gas thus formed will preferably range from about 1 to about 1.4 moles per mole, depending upon the amount of hydrogen and oxygen in the feed coal or other carbonaceous solids. The coal employed may be considered as an oxygenated hydrocarbon for purposes of describing the reaction. Wyodak coal, for example, may be considered as having the approximate formula $CH_{0.84}O_{0.20}$, based on the ultimate analysis of moisture and ash-free coal and neglecting nitrogen and sulfur. The reaction of this coal with steam to produce methane and carbon dioxide is as follows:

$$1.24H_2O(g) + 1.8CH_{0.84}O_{0.20} \rightarrow 0.8CO_2 + CH_4.$$

Under the same gasification conditions, coals of higher oxygen content will normally produce lower methane to carbon dioxide ratios and those of lower oxygen content will yield higher methane-to-carbon dioxide ratios.

The gas leaving the fluidized bed in gasifier 32 passes through the upper section of the gasifier, which serves as a disengagement zone where particles too heavy to be entrained by the gas leaving the vessel are returned to the bed. If desired, this disengagement zone may include one or more cyclone separators or the like for removing relatively large particles from the gas. The gas withdrawn from the upper part of the gasifier through line 37 will normally contain methane and carbon dioxide produced by reaction of the steam with carbon, hydrogen and carbon monoxide introduced into the gasifier as recycle gas, unreacted steam, hydrogen sulfide, ammonia and other contaminants formed from the sulfur and nitrogen contained in the feed material, and entrained fines. This gas is introduced into cyclone separator or similar device 38 for removal of the larger fines. The overhead gas then passes through line 39 into a second separator 41 where smaller particles are removed. The gas from which the solids have been separated is taken overhead from separator 41 through line 42 and the fines are discharged downward through dip legs 40 and 43. These fines may be returned to the gasifier or passed to the alkali metal recovery section of the process as discussed hereafter.

After entrained solids have been separated from the raw product gas as described above, the gas stream may be passed through suitable heat exchange equipment for the recovery of heat and then processed for the removal of acid gases. Once this has been accomplished, the remaining gas, consisting primarily of methane, hydrogen and carbon monoxide, may be cryogenically separated into a product methane stream and a recycle stream of hydrogen and carbon monoxide, which is returned to the gasifier through line 36. Conventional gas processing equipment can be used. Since a detailed description of this downstream gas processing portion of the process is not necessary for an understanding of the invention, it has been omitted.

The fluidized bed in gasifier 32 is comprised of char particles formed as the solid carbonaceous feed material undergoes gasification. The composition of the char particles will depend upon the amount of mineral matter present in the carbonaceous material fed to the gasifier, the amount of the alkali metal compound or mixture of such compounds impregnated onto the feed material, and the degree of gasification that the char particles undergo while in the fluidized bed. The lighter char particles, which will have a relatively high content of carbonaceous material, will tend to remain in the upper portion of the fluidized bed. The heavier char particles, which will contain a relatively small amount of carbonaceous material and a relatively large amount of ash and alkali metal residues will tend to migrate toward the bottom of the fluidized bed. A portion of the heavier char particles are normally withdrawn from the bottom portion of the fluidized bed in order to eliminate ash and thereby prevent it from building up within the gasifier and other vessels in the system.

The process of this invention is based in part upon the fact that the alkali metal constituents of the gasification catalyst react with the mineral constituents of the coal and other carbonaceous solids during the gasification process. Studies have indicated that at least a portion of the alkali metal compounds, such as potassium carbonate, sodium carbonate and the like, that are used as gasification catalyst constituents react with the aluminosilicates and other ash constituents to form alkali metal residues containing water soluble alkali metal compounds such as carbonates, sulfates and the like and catalytically inactive materials such as alkali metal aluminosilicates and other water insoluble compounds.

It has been found that from about 10 to about 50 percent by weight of the potassium carbonate or other alkali metal compound employed to impregnate coal or similar feed material prior to gasification will react with the aluminosilicates and other ash constituents during gasification to form alkali metal aluminosilicates and other water insoluble compounds which cannot normally be recovered from the ash by water washing. Preliminary studies tend to indicate that when potassium carbonate is utilized to impregnate the coal the major constituent of the water insoluble portion of the alkali metal residues produced is a synthetic kaliophilite, which has the chemical formula $KAlSiO_4$.

To improve the economics of the catalytic gasification process described above and other catalytic conversion processes where water insoluble alkali metal residues are formed, it is desirable to recover as much as possible of the alkali metal constituents from the insoluble residues and reuse them as catalyst constituents in the conversion process, thereby decreasing the amount of costly makeup alkali metal compounds needed. It has been found that a substantial amount of the alkali metal constituents in the water insoluble alkali metal residues withdrawn with the char and ash from the gasifier of the above-described process or the reaction zone of other conversion processes can be recovered for reuse in the conversion process by treating the particles withdrawn from the reaction zone with a calcium or magnesium-containing compound in the presence of water. The treating process is carried out under conditions such that the calcium or magnesium-containing compound liberates alkali metal constituents from the water insoluble alkali metal residues to produce an aqueous solution containing these constituents. These water soluble alkali metal constituents are then used in the conversion process as at least a portion of the alkali metal constituents which comprise the alkali metal-containing catalyst. Preferably, such use is achieved by recycling the solution directly to the conversion process. If desired, however, the alkali metal constituents may first be recovered from the solution and then used in the conversion process. The aqueous solution produced in the treatment step may contain a substantial amount of water soluble alkali metal aluminates. If such is the case, it will normally be desirable to remove the aluminum from the aqueous solution before it is recycled to the conversion process. This may be accomplished by sufficiently lowering the pH of the solution to precipitate aluminum hydroxide.

Referring again to the drawing, char particles containing carbonaceous material, ash and alkali metal residues are continuously withdrawn through line 44 from the bottom of the fluidized bed in gasifier 32. The particles flow downward through line 44 countercurrent to a stream of steam or other elutriating gas introduced through line 45. Here a preliminary separation of solids based on differences in size and density takes place. The lighter particles having a relatively large amount of carbonaceous material tend to be returned to the gasifier and the heavier particles having a relatively high content of ash and alkali metal residues continue downward through line 46 into fluidized bed withdrawal zone 47. Steam or other fluidizing gas is introduced into the bottom of the withdrawal zone through line 48 to maintain the bed in the fluidized state. Water may be introduced through line 49 in order to cool the particles and facilitate their further processing. The withdrawal rate is controlled by regulating the pressure within zone 47 by means of throttle valve 50 in overhead line 51. The gases from line 51 may be returned to the gasifier through line 52 or vented through valve 53. From vessel 47 the solid particles are passed through line 54 containing valve 55 into hopper 56.

The solid particles in hopper 56 are now ready for treatment to recover alkali metal constituents. Normally, the soluble alkali metal constituents are recovered by water washing these particles. The process of this invention, in addition to being used to recover alkali metal constituents from insoluble alkali metal residues formed during gasification or other conversion processes, may also be used to recover soluble alkali metal constituents from the water soluble alkali metal residues present in these particles. Elimination of the water wash step, however, may not be desirable since the water soluble alkali metal constituents that are normally removed in this step will be present when the particles are treated with the calcium or magnesium-containing compound and may tend to react with that compound, thereby substantially increasing the amount of the calcium or magnesium compound needed as compared to the amount that would be required if the compound was consumed only by the reactions that solubilize the alkali metal constituents from the insoluble alkali metal compounds present in the residues. Thus one of the factors in determining whether or not the water wash step should be eliminated will normally be the cost of the increased amount of calcium or magnesium-containing compound required versus the cost of the water wash step.

The process depicted in the drawing utilizes a water wash step before the particles are treated to recover alkali metal constituents or compounds from the insoluble alkali metal residues. The solid particles in hopper 56 are combined with char fines recovered from the raw product gas through dip legs 40 and 43 and line 57 and are fed through line 58 into water wash zone 59. The water wash zone will normally comprise a multistage countercurrent extraction system in which the particles are countercurrently contacted with water introduced through line 60. An aqueous solution of alkali metal compounds such as alkali metal carbonates, sulfates and the like is recovered from the unit and may be recycled through lines 61, 13, 76 and 18 to feed preparation zone 14. Here the coal or similar carbonaceous feed material is impregnated with the alkali metal compounds recovered from the soluble alkali metal residues in the water wash step and from the insoluble alkali metal residues as described hereafter.

Particles from which substantially all of the soluble alkali metal constituents have been extracted are withdrawn from the water wash zone in slurry form through line 62. Although the soluble alkali metal constituents have been removed from the particles, substantial quantities of alkali metal constituents will still be present in the form of insoluble alkali metal residues. The slurry is passed through line 62 into autoclave or similar reaction vessel 63, which is equipped with stirrer 66. Here the alkali metal aluminosilicates and other insoluble alkali metal compounds in the alkali metal residues react, in the presence of water, with a calcium or magnesium-containing compound introduced into the reactor through line 64 to form water soluble alkali metal constituents and water insoluble compounds such as calcium or magnesium silicates and the like. Apparently, the calcium or magnesium compound at least partially dissolves in the slurry water to yield calcium or magnesium ions that displace or liberate water soluble alkali metal constituents from the insoluble alkali metal compounds. The displaced alkali metal constituents are recovered in steps described hereafter and recycled to the gasification process where they serve as at least a portion of the alkali metal constituents which comprise the alkali metal-containing catalyst. Stirrer 66 is continuously operated during the reaction to at least partially prevent agglomeration of the reactants.

An example of one hydrothermal (in the presence of hot water) reaction that is believed to take place in autoclave 63 is set forth below. For purposes of writing the equation, it is assumed that a calcium-containing compound is present in the autoclave in the form of calcium hydroxide. The symbol "M" is used to represent any alkali metal cation. The actual alkali metal present will depend on the type of alkali metal compound utilized as a constituent of the alkali metal-containing gasification catalyst.

$$MAlSiO_4 + 2Ca(OH)_2 \xrightarrow[\Delta]{H_2O} MAlO_2 + Ca_2SiO_4 \downarrow + 2H_2O \quad (1)$$

-continued

 (2)

As can be seen from equation (1) above, an alkali metal aluminosilicate reacts with calcium hydroxide in the presence of hot water to yield a water soluble alkali metal aluminate, and a water insoluble dicalcium silicate. A portion of the alkali metal aluminate formed by the reaction of equation (1) will react with water to form an alkali metal hydroxide and a water insoluble precipitate of aluminum hydroxide as is shown in equation (2). The amount of the alkali metal aluminate actually found in solution will depend in part upon the temperature, pH and other reaction conditions in the autoclave. It will be understood that the above equations represent only two reactions that may take place in the autoclave. Hydrothermal reactions involving more complicated alkali metal aluminosilicates and other insoluble constituents of the alkali metal residues may also take place to form other products than those shown in the above equations.

The actual role of the water in the reactions of the calcium or magnesium-containing compound with the insoluble alkali metal residues is not definitely known. It is theorized, however, that the primary purpose of the water is to provide more favorable reaction kinetics by serving as a medium in which calcium or magnesium ions are very mobile. If the amount of water in the slurry withdrawn from the water wash zone 59 is insufficient to provide optimum kinetics, water may be added to the slurry in line 62 via line 65.

In general, the temperature in autoclave 63 will be maintained in the range between about 250° F. and about 500° F. Since the water in autoclave 63 must always be present in the liquid state to provide the medium for the hydrothermal reactions, the pressure in the autoclave should normally be equal to or greater than the vapor pressure of water at the operating temperature.

The calcium or magnesium compound used as one of the reactants in the hydrothermal reactions taking place in the autoclave may be any inorganic or organic calcium or magnesium-containing compound that at least partially ionizes or dissociates in water to yield calcium or magnesium ions. The calcium-containing compound may, for example, be calcium oxide, calcium hydroxide, calcium acetate, calcium oxalate, calcium formate, calcium carbonate, dolomine and the like. Similarly, the magnesium-containing compound may be magnesium oxide, magnesium hydroxide, magnesium acetate, magnesium oxalate, magnesium formate, magnesium carbonate, dolomite and the like. The actual calcium or magnesium-containing compound used will depend primarily upon its availability, cost and degree of solubility in water. The amount of the calcium or magnesium-containing compound needed will depend in part on the amount of silicates and soluble alkali metal constituents in the particulate matter fed to autoclave 63. If desired, a mixture of two or more calcium or magnesium-containing compounds may be used in lieu of a single compound.

The slurry effluent from reactor 63 is withdrawn through line 67 and passed to rotary filter or other solids-liquids separation device 68 where the aqueous solution containing water soluble alkali metal constituents is separated from the particulate matter and water insoluble precipitates formed by the reactions taking place in autoclave 63. Solids are removed from the filter via line 69 and will contain, among other substances, small amounts of carbonaceous material, ash, calcium silicates, and aluminum hydroxide. These solids may be disposed of as landfill or further processed to recover valuable components such as the calcium silicates which may subsequently be used in the manufacture of cement.

The aqueous effluent from filter 68 contains alkali metal constituents in solution. As can be seen from equations (1) and (2) above, these constituents will normally be comprised of alkali metal hydroxides and alkali metal aluminates. If the effluent contains only a small amount of alkali metal aluminates, it can be directly recycled to feed preparation zone 14 where the coal or similar carbonaceous feed material is impregnated with the alkali metal constituents. The recycle of the effluent may be accomplished by closing valve 83 and and passing the effluent through line 70, into line 80, through valve 81, into line 84 and through lines 76 and 18. If, however, the effluent from filter 68 contains a substantial amount of alkali metal aluminates, it will normally be desirable to remove the aluminum from solution before the aqueous effluent is recycled to the feed preparation zone. Removal of the aluminum is desirable because it may form additional alkali metal aluminosilicates in the gasifier by reacting with silica in the feed material and alkali metal constitutents of the catalyst. If removal of aluminum is desired, valve 81 is closed and the aqueous effluent from filter 68 is passed through line 70 into line 82, through valve 83 and into contactor or similar vessel 71.

In contactor 71 the pH of the effluent is lowered to a value in the range between about 10.0 and about 4.0, preferably between about 9.0 and about 5.0 by contacting it with a carbon dioxide-containing gas. The aqueous solution is passed downward through the contacting zone in the contactor at the same time as the carbon dioxide-containing gas is injected through line 72 into the bottom of the contactor. As the carbon dioxide-containing gas rises upward through the downflowing aqueous solution, the carbon dioxide in the gas reacts with the alkali metal aluminates to form alkali metal carbonates and water insoluble aluminum hydroxide. If the partial pressure of carbon dioxide is sufficiently high and the temperature in the contactor is low, alkali metal bicarbonates may also form.

A gas depleted in carbon dioxide is withdrawn overhead of contactor 71 through line 73 and either vented to the atmosphere, further processed for the recovery and reuse of carbon dioxide, or otherwise disposed of. Any carbon dioxide-containing gas, including pure carbon dioxide and air, may be used. It is preferred, however, to utilize the carbon dioxide removed from the raw product gas produced in gasifier 32. The contacting vessel utilized does not necessarily have to be of the type shown in the drawing but may be any type of vessel that allows for fairly good contacting between the carbon dioxide-containing gas and the aqueous alkali metal aluminate solution. A simple tank in which the carbon dioxide-containing gas is bubbled through the aqueous solution may be sufficient for purposes of the invention.

The purpose of the above-described step of the alkali metal recovery process is to lower the pH of the aqueous solution containing the alkali metal aluminates so that substantially all of the aluminum is removed from the solution in the form of a water insoluble precipitate of aluminum hydroxide, thereby leaving in solution aluminum-free, alkali metal constituents that are subsequently recovered and used as constituents of the gasification catalyst. As mentioned previously, removal of aluminum from the alkali metal constituents before their use in the gasification catalyst is desirable to help avoid the possible formation of additional alkali metal aluminosilicates in the gasifier by the reaction of the aluminum with silica in the feed material and alkali metal constituents of the catalyst. It will be understood that for purposes of the invention any method of lowering pH may be used. For example, instead of contacting the effluent from filter 68 with a carbon dioxide-containing gas, the effluent may be mixed with sufficient quantities of sulfuric acid, formic acid, nitric acid or the like to lower the pH to the desired value.

Referring again to the drawing, the effluent from contacting vessel 71, which contains soluble alkali metal carbonates and aluminum hydroxide, is withdrawn from the bottom of the vessel through line 74 and passed to rotary filter or other liquids-solids separation device 75. Here the solid aluminum hydroxide is removed from the aqueous solution containing alkali metal carbonates and the solution is recycled via lines 86, 76 and 18 to feed preparation zone 14 where the gasification feed material is impregnated with the alkali metal carbonates. If the concentration of alkali metal carbonates in the recycle solution is undesirably low, the solution may be concentrated by removing excess water before it is returned to the feed preparation zone. It will be understood that the exact alkali metal compound or compounds present in the recycled solution will depend on the substance used to lower the pH of the aqueous effluent from filter 68. For example, if nitric acid is used in lieu of a carbon dioxide-containing gas, the recycled solution will contain alkali metal nitrates instead of carbonates. The aluminum hydroxide collected in filter 75 may be passed through line 77 to rotary kiln or similar device 78 where it is calcined at high temperature to produce alumina, which is recovered via line 79 and may be sold as a by-product. The sale of this material may produce an additional return from the process and thus reduce the overall cost of the product gas.

The embodiment of the invention which includes the pH adjustment step is one that allows for the recovery of alumina as a by-product of the alkali metal recovery process. If recovery of alumina is undesirable for any reason, this embodiment of the invention may be simplified by eliminating filter 68 and rotary kiln 78. In such a case the slurry from autoclave 63 is passed directly to vessel 71 without liquids-solids separation and contacted with a carbon dioxide-containing gas. The effluent from the contactor is subjected to a liquids-solids separation in filter 75 and the resulting aqueous solution is recycled to the feed preparation zone. The solids, which will contain, among other substances, carbonaceous material, ash, calcium silicates and aluminum hydroxide, may be used as landfill or otherwise disposed of.

The nature and objects of the invention are further illustrated by the results of laboratory tests which indicate that soluble alkali metal compounds can be recovered from the insoluble constituents of a char produced during the catalytic gasification of a coal.

To test the effectiveness of the proposed alkali metal recovery method, a tubing bomb having a one-inch outside diameter was charged with between about five and fifteen grams of char, which was ground to smaller than 100 mesh on the U.S. Sieve Series Scale. The tubing bomb was rotated by a variable speed motor inside a tube furnace, which was equipped with a temperature controller and timer. The char was derived from the fluid bed catalytic gasification of an Illinois No. 6 coal that had been impregnated with potassium carbonate. Before the char was fed into the tubing bomb, it was analyzed for both water and acid soluble potassium. The amount of water insoluble potassium present in the char was determined by subtracting these two values. In some of the runs carried out, the feed char was washed with water before it was charged to the tubing bomb. The char was fed into the tubing bomb in the form of a slurry containing calcium hydroxide and between about 70 and about 100 milliliters of distilled water. Sufficient calcium hydroxide was used so that the slurry contained a molar ratio of calcium to potassium of between about 2.0 and about 13.0. About twenty ¼ inch carbon steel ball bearings were added to the tubing bomb to insure good agitation and to prevent caking or agglomeration. Reaction temperatures between about 350° F. and about 500° F. and reaction times between 2 and 4 hours were investigated. Solids and liquids were recovered quantitatively from the tubing bomb and separated by decanting. The solids from the bomb were washed with 150 milliliters of water and dried. Both the solids and the liquid decantant were analyzed for potassium content by means of X-ray fluorescence. The decantant was then allowed to evaporate and the resultant residue was analyzed by X-ray diffraction to determine its composition. The results of these tests are set forth below in Table I.

TABLE I

| | | | | POTASSIUM RECOVERY FROM ILLINOIS CHAR | | | | | |
|---|---|---|---|---|---|---|---|---|---|
| Run | Temperature °F. | Reaction Time (hrs) | Mole Ratio Ca/K | Water Insoluble Potassium Charged (gms) | Water Soluble Potassium Charged (gms) | Potassium In Decantant (gms) | Water Soluble Potassium In Solids (gms) | Water Insoluble Potassium In Solids (gms) | **Percent Insoluble Potassium Recovered | ***Potassium Balance Percent Off |
| 1 | 420 | 4 | 2.15 | .283 | .287 | .359 | .105 | .056 | 80.2 | −8.8 |
| 2 | 480 | 2 | 3.69 | .172 | .147 | .225 | .019 | .048 | 72.1 | −8.4 |
| 3 | 480 | 4 | 6.36 | .155 | .133 | .190 | .019 | .024 | 86.0 | −19.4 |
| 4* | 450 | 3 | 6.40 | .187 | .029 | .134 | .033 | .009 | 95.2 | −18.3 |
| 5* | 450 | 2 | 3.02 | .239 | .037 | .144 | .040 | .050 | 79.1 | −15.2 |
| 6* | 450 | 3 | 3.28 | .537 | .084 | .246 | .146 | .127 | 76.4 | −16.6 |
| 7* | 450 | 4 | 2.25 | .184 | .048 | .114 | .058 | .037 | 80.2 | −10.3 |
| 8* | 500 | 3 | 13.10 | .149 | .038 | .129 | .030 | .034 | 77.2 | +3.0 |

TABLE I-continued

POTASSIUM RECOVERY FROM ILLINOIS CHAR

| Run | Temperature °F. | Reaction Time (hrs) | Mole Ratio Ca/K | Water Insoluble Potassium Charged (gms) | Water Soluble Potassium Charged (gms) | Potassium In Decantant (gms) | Water Soluble Potassium In Solids (gms) | Water Insoluble Potassium In Solids (gms) | **Percent Insoluble Potassium Recovered | ***Potassium Balance Percent Off |
|---|---|---|---|---|---|---|---|---|---|---|
| 9 | 350 | 3 | 5.90 | .340 | .313 | .422 | .070 | .126 | 63.0 | −5.5 |

*Char was water washed to extract water soluble potassium constituents before it was charged to the tubing bomb.
**This number was calculated by dividing the difference between the water insoluble potassium charged and the water insoluble potassium found in the solids by the water insoluble potassium charged.
***This number was calculated by dividing the difference between the total amount of potassium charged and the total amount of potassium found in the liquid decantant and solids by the total amount of potassium charged.

It can be seen from Table I that the calcium hydroxide frees a substantial amount of the water insoluble potassium originally contained in the char. The percent of insoluble potassium recovered ranged from about 63 percent to about 95.2 percent and for temperatures above 420° F., the lowest percent recovery was 72.1. The relatively high discrepancies in the potassium balance for runs 3 through 6 are attributed to possible leaks in the experimental system. X-ray diffraction analyses of the residue produced from evaporation of the decantant showed the presence of $K_2CO_3$, $K_2CO_3.1\frac{1}{2}$ $H_2O$, $K_2SO_4$ and occasionally some unreacted $Ca(OH)_2$. The presence of potassium carbonate rather than potassium hydroxide is expected since the latter reacts with atmospheric carbon dioxide during evaporation of the decantant to yield the carbonate.

It will be apparent from the foregoing that the process of the invention provides an improved alkali metal recovery system, which makes it possible to significantly increase the amount of alkali metal constituents that are recovered from alkali metal residues produced during catalytic gasification and similar high temperature catalytic conversion processes. As a result, the need for costly makeup alkali metal compounds is reduced, thereby lowering the overall cost of the conversion process.

I claim:

1. In a process for the conversion of a solid carbonaceous feed material in the presence of an alkali metal-containing catalyst into liquids and/or gases wherein char particles containing carbonaceous material, ash and alkali metal residues are produced, the improvement which comprises:
   (a) treating said char particles containing said carbonaceous material, ash and alkali metal residues with a calcium or magnesium-containing compound in the presence of liquid water under conditions such that said calcium or magnesium-containing compound reacts with water-insoluble compounds in said alkali metal residues to produce an aqueous solution containing water soluble alkali metal constitutents; and
   (b) using said alkali metal constituents from said aqueous solution in said conversion process as at least a portion of the alkali metal constituents comprising said alkali metal-containing catalyst.

2. A process as defined in claim 1 wherein said conversion process comprises gasification.

3. A process as defined in claim 1 wherein said conversion process comprises liquefaction.

4. A process as defined in claim 1 wherein at least a portion of said alkali metal-containing catalyst comprises potassium carbonate.

5. A process as defined in claim 1 wherein said char particles containing said carbonaceous material, ash and alkali metal residues are treated with a calcium-containing compound.

6. A process as defined in claim 5 wherein said calcium-containing compound comprises calcium hydroxide.

7. A process as defined in claim 5 wherein said calcium-containing compound comprises calcium oxide.

8. A process as defined in claim 1 wherein said carbonaceous feed material comprises coal.

9. A process as defined in claim 1 wherein said aqueous solution is recycled to said conversion process wherein said alkali metal constituents are used as at least a portion of said alkali metal constituents comprising said alkali metal-containing catalyst.

10. In a process for the conversion of a solid carbonaceous feed material in the presence of an alkali metal-containing catalyst into liquids and/or gases wherein char particles containing carbonaceous material, ash and alkali metal residues are produced, the improvement which comprises:
   (a) treating said char particles containing said carbonaceous material, ash and alkali metal residues with a calcium-containing compound in the presence of liquid water at a temperature between about 250° F. and about 500° F. to produce an aqueous solution containing water soluble alkali metal constituents including water soluble alkali metal aluminates;
   (b) lowering the pH of said aqueous solution containing said water soluble alkali metal aluminates sufficiently to cause aluminum hydroxide to precipitate, thereby forming an aqueous solution containing water soluble alkali metal consituents substantially free of aluminum; and
   (c) using said alkali metal constituents from said aqueous solution formed in step (b) in said gasification process as at least a portion of the alkali metal constituents comprising said alkali metal-containing catalyst.

11. A process as defined in claim 10 including the additional step of water washing said char particles containing said carbonaceous material, ash and alkali metal residues before said char particles are treated with said calcium-containing compound in the presence of said liquid water.

12. A process as defined in claim 10 wherein said calcium-containing compound comprises calcium hydroxide.

13. A process as defined in claim 10 wherein said aqueous solution formed in step (b) is recycled to said gasification process where said alkali metal constituents substantially free of aluminum are used as at least a portion of said alkali metal constituents comprising said alkali metal-containing catalyst.

14. A process as defined in claim 10 wherein the pH of said aqueous solution containing said water soluble alkali metal aluminates is lowered by contacting said solution with a carbon dioxide-containing gas, thereby forming a water insoluble precipitate containing aluminum hydroxide and an aqueous solution containing water soluble alkali metal carbonates and using said alkali metal carbonates as at least a portion of said alkali metal constituents comprising said alkali metal-containing catalyst.

15. A process as defined in claim 10 wherein said alkali metal-containing catalyst comprises a carbon-alkali metal catalyst.

* * * * *